July 29, 1947. J. DE VINK Plant Pat. 748
ROSE PLANT
Filed May 31, 1946
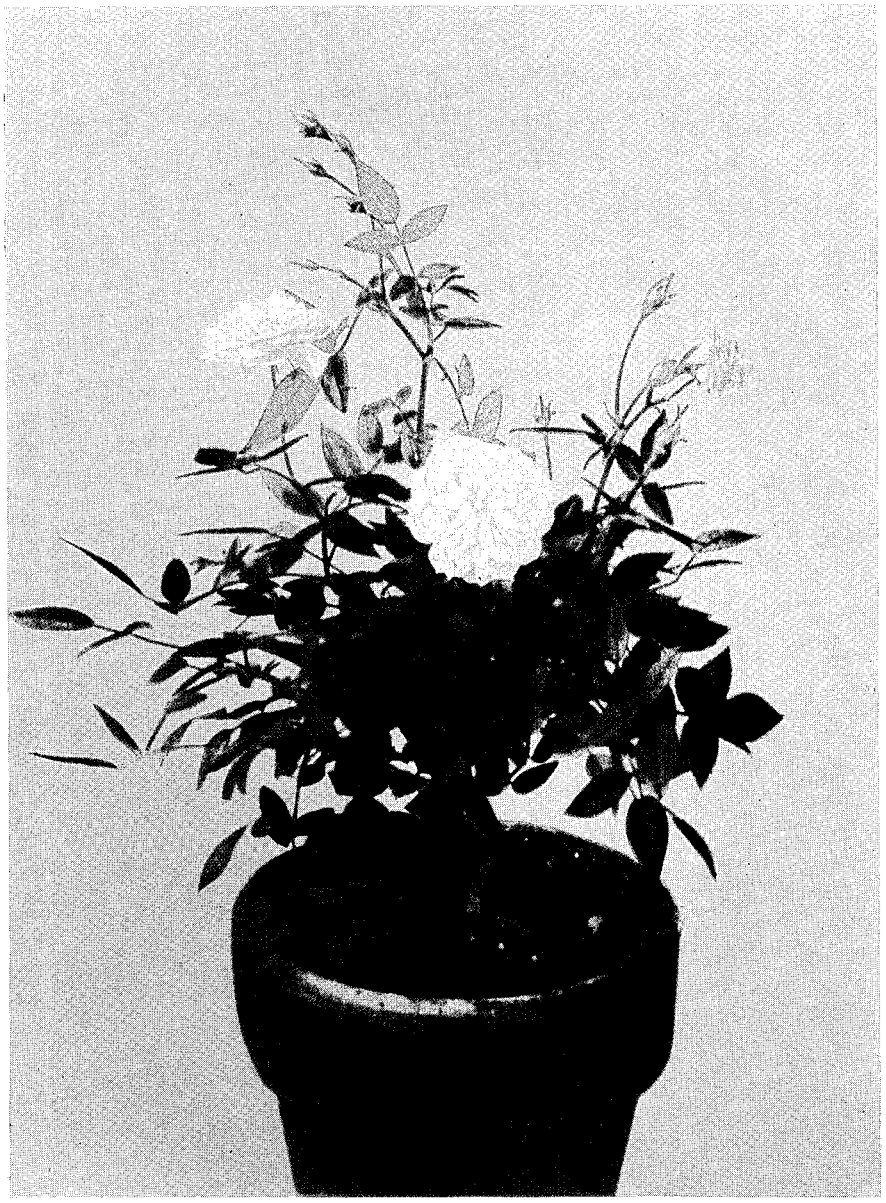
Inventor
John de Vink
By Robb & Robb
His Attorneys Patented July 29, 1947

Plant Pat. 748

UNITED STATES PATENT OFFICE

748

ROSE PLANT

John de Vink, Boskoop, Netherlands, assignor to The Conard-Pyle Company, West Grove, Pa., a corporation of Pennsylvania Application May 31, 1946, Serial No. 673,357

1 Claim. (Cl. 47—61)

The present invention relates to a new and distinct variety of rose plant in the class of miniature roses, resulting from crossing the well-known dwarf variety "Tom Thumb" (Pl. Pat. No. 169) and an unnamed seedling.

This new rose is characterized as to novelty by its hardiness and attractiveness for a plant of its class. More particularly, it is notable for the intense and penetrating fragrance of its flowers—more pervasive than found in any other roses of this group.

A further feature of novelty is found in the narrow or finer cut of the petals of the flowers and in their large number for a miniature plant of the type involved.

Predominantly, the color of the flowers of this variety, hereinafter more specifically described, is unlike any other in this class of roses of which I have knowledge.

Asexual reproduction shows that the characteristics hold true through succeeding propagations.

In the drawings there is illustrated a specimen of the plant, potted, and showing fully the foliage and the flowers in the different stages of development from bud to fully opened blooms.

The following is a detailed description of the new variety, all reference to color being in accordance with Ridgway's Color Standard and Nomenclature:

Type: Hardy; dwarf; greenhouse; outdoors; seedling.
Class: Miniature.
Parentage: Seedling.
*Seed parent.*—"Tom Thumb."
*Pollen parent.*—Unnamed seedling.
Propagation: Holds its distinguishing characteristics through succeeding propagations by cuttings, which is the only method employed up to the present time.

*Flower*

Locality where grown: West Grove, Pennsylvania.
Flowers borne: Singly and several to stem; in regular cluster; on normally strong, medium length stems.
Quantity of bloom: Free; outdoors and in greenhouse.
Continuity: Continuous.
Fragrance: Penetrating; strong rose.
Bud:
*Peduncle.*—Medium length; slender; erect; Parrot Green, Plate VI; smooth.
*Before calyx breaks.*—Size—small, about ¼ inch. Form—ovoid with a conspicuous neck; with foliaceous appendages on the surface of the bud; without foliaceous parts extending beyond the tip of the bud.
*As calyx breaks.*—Color—Tyrian Rose, Plate XIII.

*As first petal opens.*—Size—very small. Form—obovate. Color—outside—Mallow Pink, Plate XII; inside—Pale Amaranth Pink, Plate XII. Opening—opens up well.
Bloom:
*Size.*—When fully open, small; 1 inch to 1¼ inches.
*Petalage.*—Very double; 50 to 65 petals arranged regularly.
*Form.*—Cupped; high center at first; becoming open; petals at first cupped; becoming later, at maturity, loosely flat.
Petals: Thin; with inside and outside, satiny.
*Shaped.*—Outside—obovate with apex flat. Intermediate—obovate with apex flat. Inside—obovate.

This description of a newly opened flower was made from a rose grown in a greenhouse in the month of November, 1945, at West Grove, Pennsylvania:

*Color.*—*Outside petal*—outside surface—Mallow Pink, Plate XII; inside surface—Pale Amaranth Pink, Plate XII. *Intermediate petal*—outside surface—Mallow Pink, Plate XII; inside surface—Pale Amaranth Pink, Plate XII. *Inner petal*—outside surface—Mallow Pink, Plate XII; inside surface—Pale Amaranth Pink, Plate XII.

This description was made from a rose that was open for three days indoors in a greenhouse in the month of November, 1945, at West Grove, Pennsylvania:

*Color.*—*Outside petal*—outside surface—Amaranth Pink, Plate XII; inside surface—Pale Amaranth Pink, Plate XII. *Inside petal*—outside surface—Amaranth Pink, Plate XII; inside surface—Pale Amaranth Pink, Plate XII.
*General color effect.*—Newly opened flower—Pale Amaranth Pink, Plate XII. Three days open—Amaranth Pink, Plate XII.
*Behavior.*—Drop off cleanly; fading brown.
*Flower longevity.*—Grown in greenhouse kept at living room temperatures—3 days in November.

*Reproductive organs*

Stamens: Medium number; arranged regularly about pistils.
Filaments: Short; Mustard Yellow, Plate XVI; many with anthers.
Anthers: Small; Yellow.
Pistils: Medium number.
Styles: Very thin; bunched.
Stigma: Grenadine Pink, Plate II.
Ovaries: All enclosed in calyx.
Hips: Oblong, with neck pear-shaped; Parrot Green, Plate VI; smooth; walls thin.
Sepals: Moderately long; recurved.

*Plant*

Foliage:

*Leaves.*—Compound of 3, 5, 7, many leaflets; normal in amount; very small; moderately thin.

*Leaflets.* — Shape — lanceolate with apex acute.

*Color.* — *Mature* — upper surface — Normal Hellebore Green, Plate XVII; under surface—Light Bice Green, Plate XVII. *Young* — upper surface — Light Lettuce Green, Plate V; under surface—Parrot Green, Plate VI.

*Rachis.* — Light. Upper side, smooth, grooved; under side, sparsely thorny.

*Stipules.*—Medium length; narrow; with short points turning out at an angle of less than 45°.

*Disease.*—Good resistance.

Growth:

*Habit.*—Dwarf; bushy; much branched.

*Growth.*—Free.

*Canes.*—Light.

*Main stems.*—Dull Parrot Green, Plate VI. *Thorns*—few; short; straight; with narrow base. *Prickles*—none. *Hairs*—none.

*Branches.*—Dull Parrot Green, Plate VI. *Thorns*—none. *Prickles*—none. *Hairs*—none.

*New Shoots.*—Bright Mahogany Red, Plate II. *Thorns* — none. *Prickles* — none. *Hairs*—none.

I claim:

A new and distinct variety of rose plant of the dwarf class, characterized as to novelty by its hardiness, the intense and penetrating fragrance of its flowers, the numerous petals and narrow cut thereof, and the pink coloring of the flowers, substantially as shown and described.

JOHN DE VINK.